United States Patent [19]
DiLullo

[11] Patent Number: 4,735,199
[45] Date of Patent: Apr. 5, 1988

[54] DREAM DETECTION METHOD AND SYSTEM

[76] Inventor: John D. DiLullo, 116 Ferguson Ave., Broomall, Pa. 19008

[21] Appl. No.: 818,877

[22] Filed: Jan. 14, 1986

[51] Int. Cl.⁴ .............................................. A61B 19/00
[52] U.S. Cl. .................................. 128/1 R; 128/731; 128/782
[58] Field of Search ............... 128/630, 670, 731, 774, 128/782, 1 R

[56] References Cited

U.S. PATENT DOCUMENTS

| | | | |
|---|---|---|---|
| 3,955,562 | 5/1976 | Farrar, Jr. | 128/2 S |
| 4,228,806 | 10/1980 | Lidow | 128/731 |
| 4,381,504 | 4/1983 | Bitko | 340/689 |
| 4,420,001 | 12/1983 | Hearne | 128/724 |
| 4,450,326 | 5/1984 | Ledger | 200/61.45 |

OTHER PUBLICATIONS

"Ethology of Sleep Studied with Time-Lapse Photography: Postural Immobility and Sleep-Cycle Phase in Humans", Hobson et al., Science, vol. 201, 1978, pp. 1251-1253.
"Every 90 Minutes a Brainstorm", Michael Chase, Psychology Today, Nov. 1979, p. 172.
Sleep and Dreaming, D. Cohen, pp. 176-181 (Great Britain: A. Wheaton and Company, Ltd., 1979).
Advances in Dream Research, Elliot Weitzman, "Summary of Findings of Dement and Kleitzman, 1957" (New York: Spectrum Publications, 1976).
Sleep Dreams and Arousal, Edward J. Murray, pp. 40-41 (New York: Appleton-Century-Crofts, 1965).
"Lucid Dreaming", S. P. LaBerge, Psychology Today, Jan. 1981, pp. 48-57.
"Build a Voice Operated Switch for Your Tape Recorder", J. P. Reed, Radio Electronics, Nov. 1983.
99 Practical Electronic Projects, Herbert Friedman, pp. 113-114 (Indiana: Howard W. Sams and Co., Inc., 1971).

Primary Examiner—Kyle L. Howell
Assistant Examiner—Randy Citrin
Attorney, Agent, or Firm—Ratner & Prestia

[57] ABSTRACT

The present invention relates to a dream retrieval method and system including the physiological monitoring of a sleeping subject, the analysis of recurring behavioral parameters, the application of suitable algorithms to the observed parameters and, subject stimulation in response to algorithm deductions. In the preferred embodiment, gross body motions and postural changes are both analyzed in magnitude and regularity. Upon recognizing recurring body motions indicative of a dream cycle, the device establishes a time window during which the completion of the next dream should occur. If physiological behavior indicative of dreaming is discovered within the time window, the subject is awakened. As a result of this timely awakening, the subject obtains greater dream recall than is normally possible and may optionally record dream content.

8 Claims, 5 Drawing Sheets

DREAM DETECTION METHOD AND SYSTEM

BACKGROUND OF THE INVENTION

A. Field of the Invention

This invention relates to increasing dream recall and more specifically to increasing dream recall by awakening a subject immediately after a dream.

B. Background Art

Throughout the period of sleep, humans typically experience dream periods. Dream periods (REM) comprise approximately 15%–20% of the evening's sleep and occur with regularity every 80–100 minutes. While the subject is asleep, however, the body continues to exhibit many characteristic physiological changes. Although most of these changes are readily monitored and calibrated, the preferred embodiment focuses on the subject's motor activity which occurs during sleep. For instance, during sleep there are frequent gross body movements or postural changes. These shifts in position occur with increased frequency before and after dream periods, whereas a period of simulated paralysis occurs during the dream period proper. As a specific example, during human sleep there is a period of increased motor activity before a dream, a period of relative immobility during the dream, and increased motor activity following the dream. This behavior is then repeated 80–100 minutes later. Prior art, such as "Ethology of Sleep Studied with Time-Lapse Photography: Postural Immobility and Sleep-Cycle Phase in Humans" by Hobson in *Science*, Vol. 201, 1978, pp 1251–1253, includes the analysis of postural changes during sleep and acknowledges the regularity of dreaming but, never has a means for the utilization and calibration of gross body movements in predicting dream occurrences been disclosed. This is also discussed in *Advances in Dream Research* by Elliot Weitzman, Spectrum Publications, 1976.

During an average sleeping period, the sleep-dream cycle repeats 4–6 times as noted in "Every 90 Minutes, A Brainstorm" by Michael H Chase, *Psychology Today*, November 1979, p. 172. The percentage of dreams recalled and the accuracy with which they are recalled varies between individuals but, dream content is usually forgotten unless the individual has been awakened or disturbed during the dream. To effectively capture dream content it is therefore desirable to awaken a subject at the conclusion of his dream as recognized in *Sleep and Dreaming* by David B. Cohen, A. Wheaton and Co., Ltd., 1979.

Many prior patents have been obtained for the awakening of a subject in response to the monitoring of brain wave activity which would indicate that a subject is falling asleep. These systems have obvious use in the awakening of a dozing driver or the monitoring of patients in an intensive care situation. U.S. Pat. No. 4,228,806 discloses a device which inhibits wake-up alarms during deeper phases of sleep; thus functioning as an alarm clock accessory which prevents the subject from being aroused from a deep sleep. There is no attempt, however, in these prior art arrangements to address dream retrieval or a means of automated calibration or correlation of gross body movements found near and about dream periods.

Obvious to those in the field is the possible alteration of dream content by the introduction of physical stimuli to a dreaming individual. Prior art includes devices which dictate suggestions to sleeping individuals at some predetermined time into the period of sleep. However, these devices do not calculate when the subject is dreaming and only provide for random application of subject stimuli. See for example "Lucid Dreaming" by Stephen LaBerge in *Psychology Today*, January 1981, pp. 48–57.

British Pat. No. 1,215,904 and U.S. Pat. No. 4,420,011 disclose devices which measure increased respiration during "unpleasant dreams," after which, an attempt is made to bring the subject to a higher level of consciousness where they might experience a more "lucid" dream. These references lack the correlation of findings from earlier in the sleeping period to more recent subject behavior in the predicting and ultimate retrieval of their dreams.

Motion sensors function in various systems and devices not related to human movement. U.S. Pat. Nos. 4,381,504 and 4,450,326, both disclose devices which establish electrical continuity across two or more terminals when translated or displaced. However, neither of these embodiments measure or correlate the intensity of sound produced during the actual motion. U.S. Pat. No. 3,955,562 depicts a device for measuring the degree of positional change found in normal human movement but pertains only to the connection of electrical contacts by the depression of switches or translation of electrically conductive fluid.

BRIEF DESCRIPTION OF THE INVENTION

The present invention provides a method and system for confirming the occurrence of dream behavior in a sleeping subject. The subject is monitored for an initial occurrence of physiological behavior indicative of dream sleep. After apparent dream behavior is recognized, a wait period, equal to the typical duration between two successive dreams, is initiated. After this period, a recurrence of previous dream behavior is sought. Upon detecting the second occurrence of the dream behavior, the present invention confirms the occurrence of a dream cycle.

More particularly, the present invention embodies a dream retrieval system for analyzing gross body movements, calculating dream periods, extrapolating from these periods projected dream occurrences, and finally awakening the subject upon the conclusion of a dream. A further embodiment provides methods of dream alteration or enhancement. Physical and/or auditory stimuli may optionally be given to the subject once a dream occurrence has been established in an attempt to constructively interfere with dream content. The auditory stimuli may include a tone or pulse in the audible frequency range of sufficient volume to be heard by the subject. This dream enhancement function will hereinafter be referred to as "the suggester". The suggester may be a tape player or a siren.

Motion sensors, attached to the subject or sleeping surface, detect body motion and using a short-range transmitter relay information to a receiver where they are calibrated, qualified, and then forwarded to the input port of a computation device. Once the motions have been encoded, the train of pulses is searched and analyzed for periods of increased movement frequency. Once increased movement frequency indicative of pre-dream conditions is noted, a period of relative immobility followed by motions indicative of a post-dream condition are searched for. If these conditions are satisfied, an apparent dreaming epoch has occurred. A sleep-dream cycle is confirmed if a recurrence of these motion conditions occurs 80–100 minutes later. After this confirmation, dream manipulation may be performed followed by subject awakening. A tape recorder may be supplied at the sleep site for the subject to record dream content.

The parameters which qualify a group of motions as being either pre-dream or post-dream in nature may be adjusted to best satisfy the particular characteristics of the individual. In addition, the dream enhancement routines which physically prompt and stimulate the sleeping subject, operate independent from the post-dream awakening mechanism. Hence, these are optionally engaged or interchanged, depending on the subject's favor.

DETAILED DESCRIPTION OF THE DRAWINGS

Figure 1A:
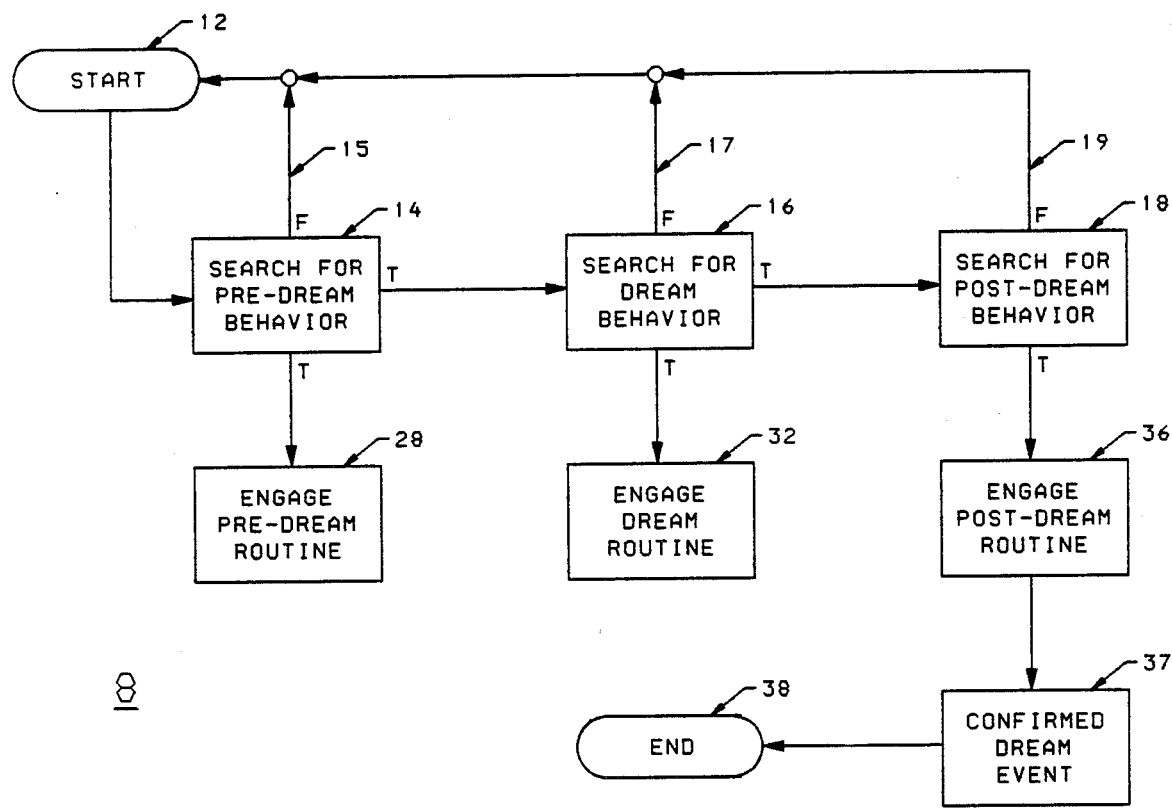
FIGS. 1A,B are block diagrams which illustrate the determination of dream periods by applying typical dream recurrence parameters.

Referring to FIGS. 1A,B there is shown block diagrams of the dream retrieval system of the present invention. System 8 is essentially geared toward accurately predicting dream periods by detecting physiological behavioral patterns. System 8 divides each dream event into three separate units; pre-dream sleep, dream sleep, and post-dream sleep. The system evaluates each unit independently and anticipates physiological behavior unique to that phase of sleep.

At start block 12, system 8 allows the subject to fall asleep. This is executed by either allotting the subject a predetermined period of time to fall asleep or by awaiting certain physiological conditions which indicate that the subject is asleep. System 8 searches at block 14 for subject behavior parameters indicative of pre-dream sleep. Physiological pre-dream behavior parameters may include, for example, increased brain-wave activity, moderate increases in respiration, increased muscle tonus, and increased limb movement in connection with postural shifts and gross body motions. Once the pre-dream behavior of block 14 is established, optionally the pre-dream routine of block 28 may be engaged. This routine may contain, for example, an alarm or other stimuli to awaken the subject, thus enabling dream deprivation or the exploration of other various pre-dream fields of interest.

Control is then transferred to block 16 where a determination is made whether the subject is dreaming. Physiological conditions, indicative of dreaming may include, for example, rapid eye movements (REM), increased respiration rates, electro-neural activity, muscle tonus, extremity twitching, and simulated spinal paralysis. Once dreaming behavior of block 16 has been established, optionally, the dream routine of block 32 may be engaged. This routine may contain, for example, a dream enhancement mode which would attempt to alter or contaminate a subject's dream through the introduction of pseudo-hypnotic suggestion or sleeping environment manipulation. Other dream routines might include, for example, a "lucid" dream inducer or a mid-dream interrupter. In addition, physical promptings and possible methods of bio-feedback, incorporating monitored physiological responses, may also be employed, as they might also affect dream content. After such intervention the subject may optionally be awakened or allowed to continue sleeping.

Control is then transferred to block 18 where a determination is made whether the subject is experiencing post-dream sleep. Physiological conditions indicative of post-dream sleep may include, for example, an abrupt drop in electro-neural activity, decreases in respiration rates, and a rebound or increase in limb movements possibly accompanied by postural shifts and gross body motions. Once the post-dream behavior in block 18 has been established, the post dream routine of block 36 may be engaged. In the embodiment of dream retrieval system 8 the subject is awakened upon dream completion, thus permitting dream recall. The subject may then verbally or otherwise record dream content on a tape recorder (not shown). Furthermore, upon acknowledging the completion of the dream at block 18, system 8 may implement bio-feedback methods to possibly lengthen the dream itself.

Control is then transferred to block 37 where system 8 confirms that a dream event has transpired. System 8 may terminate at block 38 or may return to start block 12.

It should be noted, that in establishing an apparent dream event some blocks of FIG. 1A may be omitted. For example, a dream event may be established on the basis of the pre-dream sleep behavior determined in block 14 and/or the post-dream sleep behavior determined in block 18. In this case, system 8 can still confirm the dream event at block 37 without recognition of the subject's physiological behavior during the dream period at block 16. This ability becomes especially useful when measuring gross body movements during sleep, as there are no characteristic body movements inherent in dream sleep. In this case, block 16 is bypassed. Further, by way of lines 15, 17, and 19 if the corresponding conditions of blocks 14, 16, and 18, respectively, are not satisfied, control is returned to start block 12 and the current dream event that system 8 was tracking is invalidated.

Figure 1B:
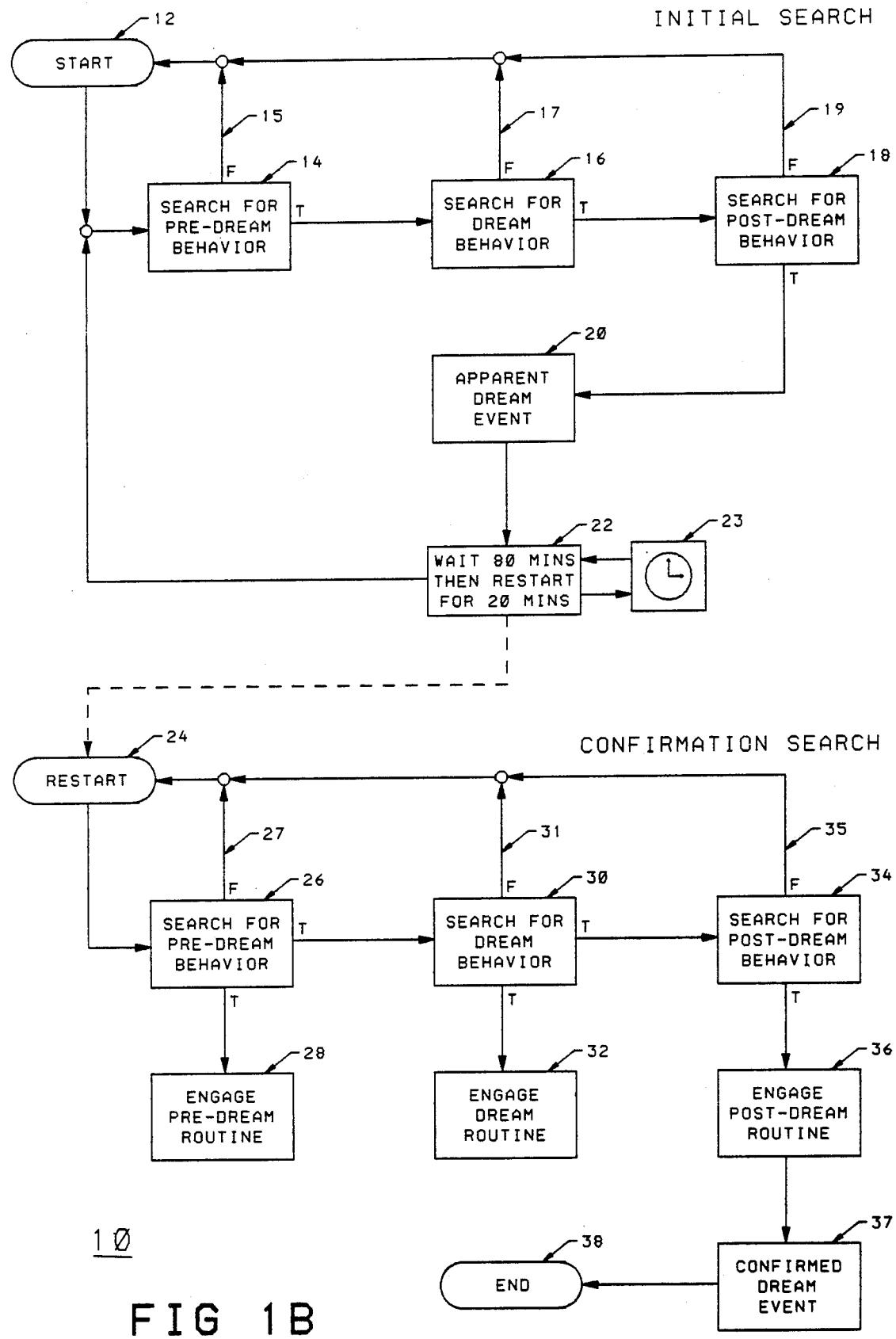

Referring to FIG. 1B there is shown a block diagram of dream retrieval system 10 in which a method for confirming the dream determined by system 8 is provided. This method for confirming the occurrence of a dream is based upon the cyclical nature of dream behavior.

System 10 which is the preferred embodiment of the present invention uses the same behavioral patterns to determine dream periods as system 8 but, including a calibration function which identifies a recurrence of the dream cycle. As in system 8, blocks 14, 16, 18 search for pre-dream, mid-dream and post-dream physiological behavior respectively. System 10, however, does not immediately engage routines 28, 32, and 36 as previously described for system 8. Instead of confirming the dream event immediately after the post-dream behavioral parameters are observed in block 18, at block 20 an apparent dream is determined and the confirmation of a dream event in block 37 is not performed until later in the sleep period.

When an apparent dream event is established at block 20, an appropriate waiting period is initiated at block 22. This "waiting period" and all other timing parameters relative to block 22 are obtained from peripheral clock 23. Since dreams recur in a cyclic fashion, system 10 allows time for the non-dream phases of sleep to transpire. Therefore, system 10 does not anticipate a recurrence of an apparent dream event, as found in block 20, until later in the sleep cycle. Therefore, a time window is established approximately 80 to 100 minutes after the determination of an apparent dream event in block 20. Hence, after 80 minutes, system 10 expects another dream event which physiologically resembles the first apparent dream event detected at block 20. After 100 minutes, however, if system 10 has not detected a second dream event, the window ends and control returns to start block 12, as the dream sleep parameter has expired. During this wait period, however, system 10 may engage deep-sleep stimuli or physical promptings as the subject is still being monitored and thus may still interact with the machine.

After waiting 80 minutes in block 22, control is transferred to restart block 24 where the search for a dream event recurrence begins. At block 26, a determination is made whether the subject is experiencing pre-dream sleep. Physiological conditions that would indicate pre-dream sleep include those conditions observed as pre-dream behavior at block 14. If pre-dream behavior is detected at block 26 and, since the subject has demonstrated recurring physiological behavior; pre-dream sleep is confirmed. Optionally, at block 28 the pre-dream routine previously described in system 8 may be engaged.

Once the pre-dream behavior of block 26 is established, control is transferred to block 30 where a determination is made whether the subject is experiencing dream sleep. Physiological conditions that indicate dream sleep include those observed as recurrent from dream behavior at block 16. If dream behavior is detected at block 30 and, since the subject has demonstrated recurring physiological behavior; dream sleep is confirmed. Optionally, at block 32 the dream routine previously described in system 8 may be engaged.

Once the dream behavior of block 30 is established, control is transferred to block 34 where a determination is made whether the subject is experiencing post-dream sleep. Physiological conditions that indicate post-dream sleep include those observed as recurrent from post-dream behavior at block 18. If post-dream behavior is noted at block 34 and, since the subject has demonstrated recurring physiological behavior; post-dream sleep is confirmed. Optionally, at block 36 the post-dream routine described in system 8 may be engaged.

After the completion of the post-dream routine in block 36, system 10 determines at block 37 that a confirmed dream event has transpired. Subsequently, system 10 ends at block 38. Here, since the subject has been aroused, system 10 may be entirely aborted or control may simply return to start block 12. If, however, the subject is only mildly aroused, control may simply return to block 22, as a dream event similar to that in block 20 has just been confirmed at block 37.

It should also be noted that by way of lines 27, 31, or 35 if the conditions of blocks 26, 30, or 34, respectively, are not satisfied, then an entire dream event as in block 20 is not confirmed and control is transferred to restart 24. Further, if control is still at block 24 when the time of block 22 exceeds minute 100, a start is instituted at block 12, as the recurrence parameter was exceeded.

Figure 2:
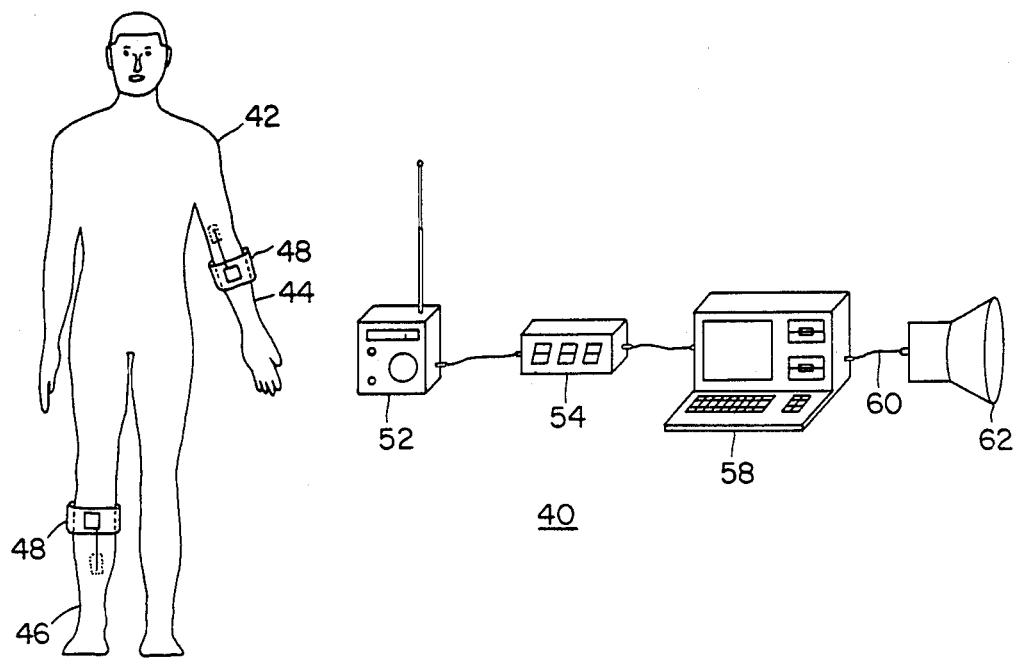
FIG. 2 is a pictorial representation of hardware devices of the preferred embodiment of the invention of FIGS. 1A,B.

Referring to FIG. 2 there is shown the preferred physical arrangement of the hardware devices of dream retrieval system 40. Subject 42, in the manner one might wear a bracelet or bandage, has fastened to forearm 44 and calf 46 sensor bands 48 which detect subject motion. Sensor bands 48 relay to a conventional receiver 52 information pertaining to the motion of subject 42. Input collected by receiver 52 is forwarded to calibration unit 54 which analyzes the intensity of the motions. In this application, calibration unit 54 consists of an audio level meter similar to those used in stereophonic equipment. If an incoming signal reaches or exceeds a predetermined decibel value, the signal is qualified as a gross body movement, and a clean, conditioned signal is sent to data processor 58 for compilation. The listing of the program for data processor 58 appears at the end of the specification as an appendix and is written in a structured format (FORTRAN-77) understandable to those of ordinary skill in the art. Subject arousal device 62 is engaged directly from an annunciating port of data processor 58 by way of line 60.

Figure 3A:
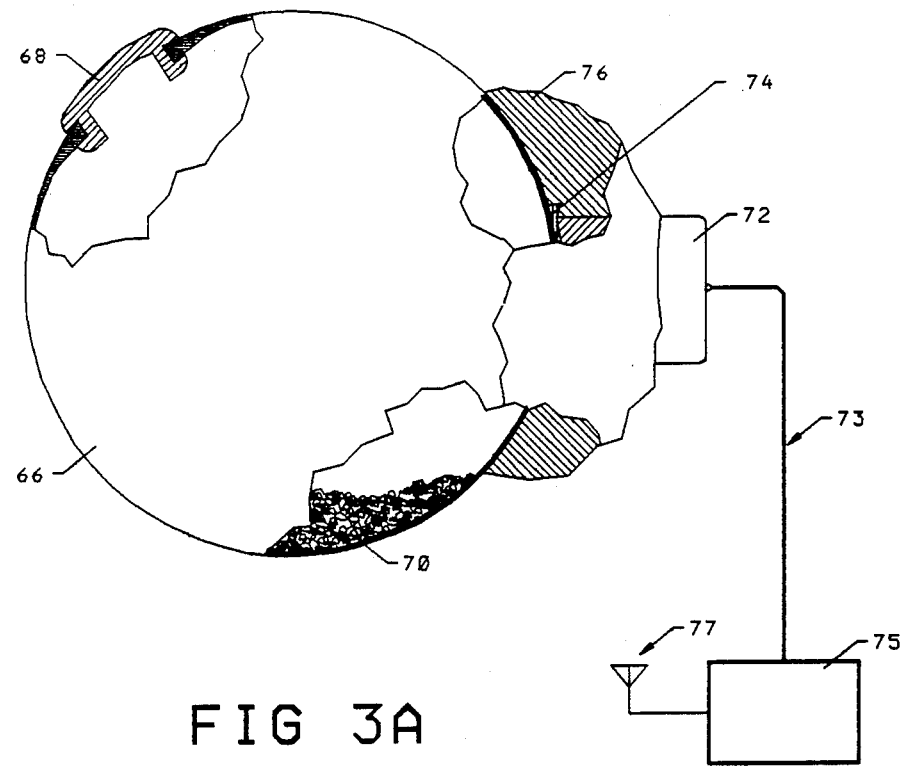
FIGS. 3A,B illustrate the preferred embodiments of the motion sensor and its appropriate means of attachment to the subject.

Referring to FIG. 3A there is shown the preferred embodiment of motion sensor 64 which may be contained within sensor bands 48. Motion sensor 64 consists of a hard plastic, spherical shell or "bulb" 66 which is sealed by plug 68 of similar material. This permits the implant of irregularly shaped nuggets 70 within bulb 66. Nuggets 70 may consist of steel punching chips or similar material. A dynamic microphone 72 is mounted directly to the outer surface of hollow bulb 66, physically separated by a small piece of acoustically transparent felt 74. Felt 74 deadens sound which might result from microphone 72 rubbing against bulb 66, thus, preventing these sounds from being interpreted as motions of subject 42. Microphone 72 is mounted on bulb 66 using a quick setting, molded epoxy cement 76. This mounting is, however, not the only means for microphone 72 attachment, as it might just as effectively be mounted with bulb 66 by other means. Further, it should be noted that motion bulb 66 may be formed in any convenient size, as it will not affect the actual function of hardware system 40.

When a motion occurs, motion sensor 64 reacts in the following manner: As bulb 66 is displaced or translated nuggets or punching chips 70 collide with each other and against the inside wall of bulb 66. This produces a rattle-like sound which microphone 72 detects and, by way of wire 73 relays to transmitter 75. Wire 73 is any 18–22 A.W.G. shielded microphone cable or could equivalently be replaced by shielded copper contacts if transmitter 75 is physically attached to bulb 66. Transmitter 75 comprises a radio transmitter of compact design powered by a miniature battery or other conventional electric cell.

Circuitry used to transmit and calibrate the various levels of sound measurable by the system is described in 99 *Practical Electronic Projects*, pg. 113; and similarly by a circuit disclosed in the publication "Radio Electronics", November 1983, entitled "Build a Voice Operated Switch for Your Tape Recorder." Additionally, circuitry and other details relevant to the present invention are described in "The Dream Retrieval System" by John Dilullo published at the American Society for Mechanical Engineering Convention in Atlanta, Georgia, June 16, 1985, which is incorporated herewith by reference. However, any conventional audio output meter would suffice. Radio waves are carried from transmitter 75 by antenna 77 which may be a cylindrical conductor or simply a singular strand of 20 A.W.G. solid copper wire. Antenna 77 may dangle freely from transmitter 75 or optionally may be sewn directly into sensor bands 48.

Figure 3B:
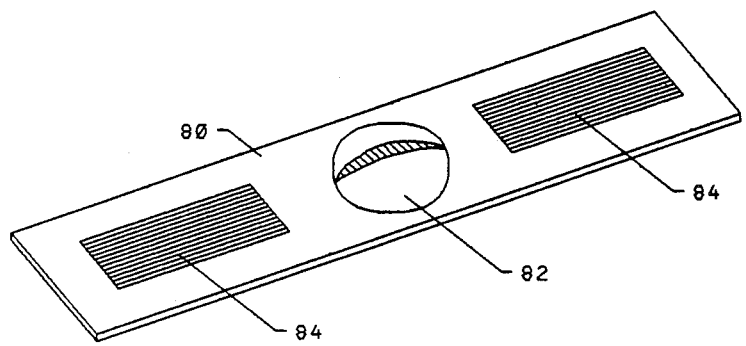

Referring to FIG. 3B there is shown band 48 which is the preferred means of attaching motion sensor 64 to subject 42. Sensor band 48 consists of a double pleated, flexible plastic strip 80 with a singular small cavity 82. Cavity 82 snugly houses motion bulb 66. Band 48 wraps around forearm 44 or calf 46 of subject 42 and may be fastened with institched Velcro 84. This embodiment, however, is not the only method of attaching motion bulb 66 to subject 42. Motion bulb 66 may be sewn directly into the subjects clothing or may alternately be affixed to the sleeping surface.

Figure 4:
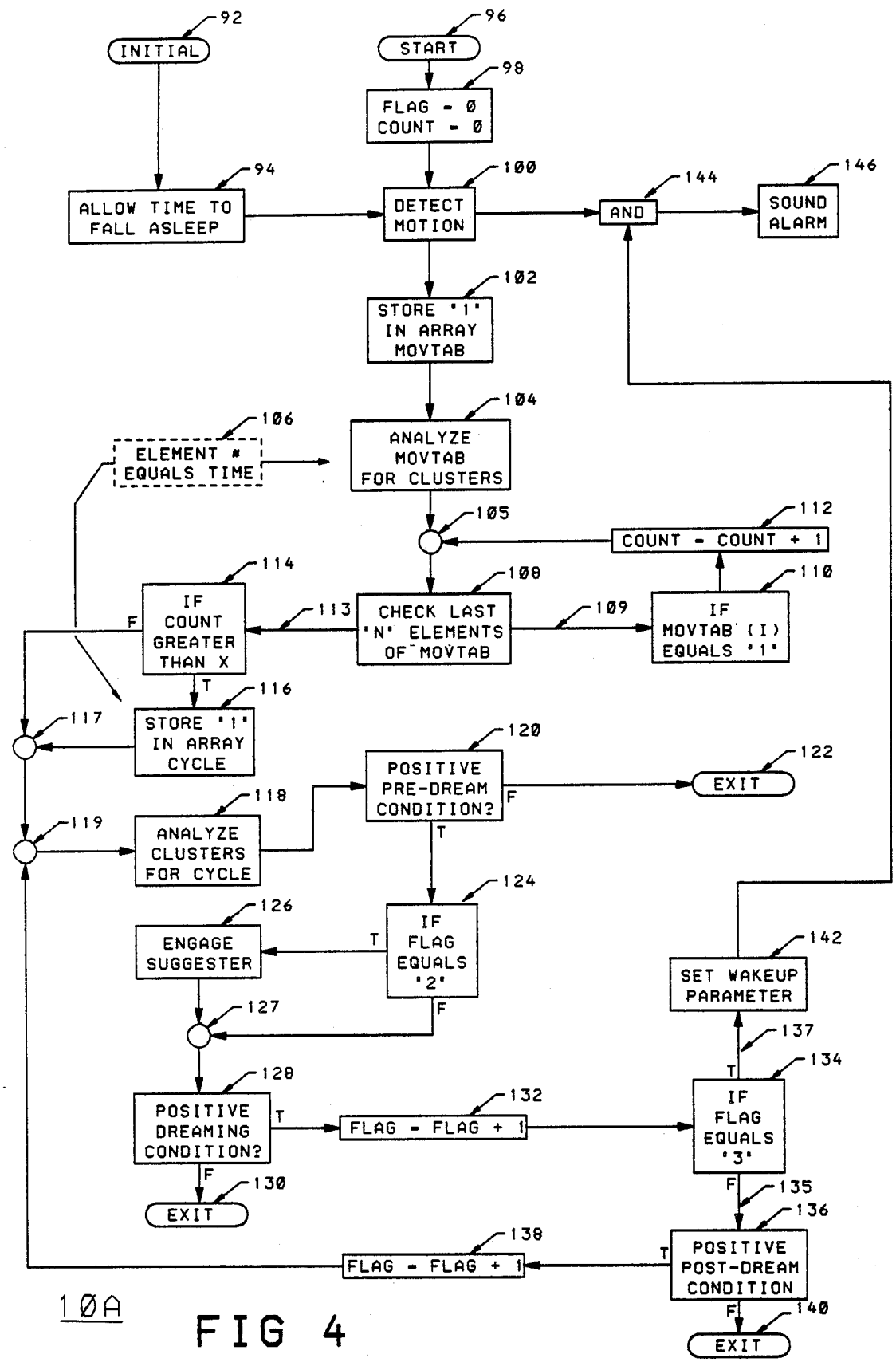
FIG. 4 is a flow chart which shows the logic of a FORTRAN program which implements the preferred embodiment.

Referring to FIG. 4 there is shown system 10a which is a more detailed representation of system 10. System 10a records, calibrates, and extrapolates the cyclic body motions which recur during human sleep. From these cyclic body motions, three subdivisions of dream sleep are identified: pre-dream sleep, dream sleep, and post-dream sleep. With a few modifications, however, system 10a could comprise, in combination, a device which applies many aspects of physiological behavior in determining dream periods. Using conventional interfacing techniques the present invention could monitor and record, for example, electro-neural activity, respiration, rapid eye movements, muscle twitches, and perspiration.

In the present embodiment of system 10a the device is set to engage a suggester during a confirmed dream event and subsequently awaken the subject following that dream event. Thus, system 10a functions as a dream enhancement and retrieval system.

When system 10a is initially engaged, execution begins at initial block 92 where system 10a assumes that subject 42 has just retired and will need time to fall asleep. System 10a is not concerned with pre-sleep motion and, therefore, at block 94 an arbitrary wait period is allocated to allow subject 42 time to fall asleep. Furthermore, in the description of start block 12 of system 10, numerous methods are described for determining when subject 42 is asleep. Block 94 is only executed once because all exits and resetting transfers of execution are forwarded to start block 96. Start block 96 differs from initial block 92 in that no dozing parameter is initiated. This is acceptable since at block 96 subject 42 is already assumed to be sleeping.

When execution reaches start block 96, system 10a assumes that somewhere within the body of the program conditions have warranted either an exit or a formal abort. Therefore, any flags which have been set or any counts which have been registered, are no longer valid and are reset to zero. As set forth in paragraph three of the Appendix, this zeroing function is performed at block 98, where the flags and counting variables are zeroed. In block 100 a determination is made whether a motion has occurred. Motion pulses are input from calibration unit 54 and are in the form of an analog "1." When a valid motion is received, block 102 assigns an integer value of "1" to an element of the array MOVTAB, as set forth in paragraph seven of the listing.

The element number of MOVTAB is determined by the current time as obtained from block 106. When called, block 106 returns a three digit integer value. This value is an expression, in minutes, of the current time, where, for example, the time at initial block 92 equals 000. After block 106 is referenced execution always returns directly to the location where block 106 was called. The array MOVTAB is therefore a tabulation of the evening's motion, where each element represents one minute of sleep. Accordingly, each element of MOVTAB which contains an integer value of "1" represents a particular minute of sleep where subject 42 had at least one gross body motion.

Since pre-dream sleep and post-dream sleep both share an increase in gross motor activity, at block 104 system 10a searches for motion flurries or clusters. A cluster is formally defined as a specified number of motions occurring within a specified period of time. When both the duration and count parameters are satisfied, a motion cluster is established. Typical parameters representative of a cluster are, for example, four movements within eight minutes or three movements within six minutes. Here, the number of movements and the period of time could be easily manipulated to an individual's particular sleeping characteristics and peculiarities.

The analysis described in block 104 is executed in blocks 108 through 112. Block 108 begins the retrospective analysis of the array MOVTAB for motion clusters. This process is performed by testing the last N elements of the MOVTAB array. N equals the pre-specified time parameter, in minutes, of the duration of a typical motion cluster. When searching for motions indicative of pre-dream sleep, N equals the variable IPREPR in the Appendix whereas when searching for motions indicative of post-dream sleep N equals the variable IPOSPR as specified in paragraph seven of the Appendix. By way of line 109, block 110 examines the Ith element of the MOVTAB array and determines when a motion has occurred. In this application I is an integer variable whose value increases by an integer increment of 1 each time a new element of MOVTAB is referenced. I is initialized as the integer value of the current time, less the value of the duration parameter N. The loop is aborted when I reaches the value of the current time. If, during this analysis, a specific element of MOVTAB contains a motion, block 112 is referenced and the current count is increased by one. Depicted in paragraph eight of the listing, this process of sorting and accumulating is continued until the last N elements of MOVTAB have been analyzed. After this, control returns to junction 105.

After analyzing MOVTAB for clusters, control is taken to block 114 by way of line 113. At block 114 a determination is made whether the number of motions found in the last N elements of MOVTAB qualify as a cluster in accordance with the pre-determined time and count parameters. This process compares the current count to a pre-determined count variable X. X equals the integer value of the specified count parameter of a typical motion cluster. Pre-dream specifications denote X as equaling the variable IPRCNT and post-dream specifications denote X as equaling the variable IPOSCT, as set forth in paragraph eight of the listing. As is apparent, both N and X could easily be manipulated thus altering the qualifying parameters of a motion cluster and adding a method of adjustability to system 10a.

If a group of motions from block 108 qualifies as a cluster as determined in block 14, an integer value of "1" is stored in the CYCLE array at block 116. The CYCLE array appears equivalently in paragraph nine of the appendix as the array NCYCLE, however, its function is identical. The element number of NCYCLE is determined by the integer representation of the current time as obtained from block 106. After this assignment, system 10a moves to junction 117. If it is determined in block 114 that the count obtained in 108 is not sufficient to indicate a motion cluster, block 116 is bypassed and execution moves directly to junction 117. In either case, from junction 117 execution moves to junction 119 and then to block 118 where the process of analyzing the NCYCLE array for recurrent clusters is initiated.

The NCYCLE array is analyzed with the following considerations: Pre-dream motion clusters are represented with an integer value 1 in the row dimension of the array while post-dream motion clusters are represented with an integer value 1 in the column dimension of the array. When block 118 is referenced system 10a searches for 1's in the NCYCLE array. In addition since the NCYCLE array element numbers are assigned integer values equivalent to the time of their occurrence, an analysis of the NCYCLE array 80-100 elements prior to the current time at block 106 is performed. Thus a current dream event can be confirmed by determining that a cluster of motions preceded the current cluster of motions by an amount of time approximately equal to that of a dream cycle.

In summary, block 118 initiates the search for an integer value of 1 in the row dimension of NCYCLE. A 1 indicates a pre-dream motion cluster. Execution then sorts and accumulates 15-30 consecutive elements of NCYCLE. If the final value of the accumulator is 0, no motion clusters appeared during the apparent dream period, thus confirming a period of relative immobility. Next, NCYCLE is searched for an integer value of 1 in the column dimension. If found, post-dream behavior is confirmed and an apparent dream event has been observed. A similar occurrence will be searched for the NCYCLE array 80-100 elements past the row element which initially indicated pre-dream motion. This search for recurrence is set forth by the listing in paragraph nine.

To determine whether initial or recurrent behavior is being monitored, a flag system is used. Each time dream behavior is noted at block 128 the flag is increased by an integer value of 1 and, similarly, each time post-dream behavior is noted at block 136 the flag is increased by an integer value of 1. Hence, after the first run through the loop, if both pre-dream and post-dream conditions are noted, the flag equals the integer value 2. If the dreaming condition is confirmed again the flag will increase to 3. Thus, the purpose of the decisions at blocks 124 and 134 is to determine whether recurrent behavior is being observed.

Similar to the procedure in block 14 of system 10, block 120 determines whether subject 42 is experiencing motion behavior indicative of pre-dream sleep. When an integer value of 1 is found in the row dimension of the NCYCLE array a pre-dream condition is confirmed. But, if the conditions at block 120 are not satisfied, control moves to block 122 where an exit is encountered and execution is subsequently transferred to start block 96. If, however, the conditions mentioned above are established in block 120, execution moves to block 124 where a determination is made whether the flag equals the integer value 2. If the flag equals the integer value 2 then a recurrence of pre-dream sleep has been observed and the suggester of block 126 may optionally be engaged. Subsequently, when the flag equals some integer value less than 2 the following deduction is made: no previous flags have been set and this pre-dream condition is without confirmation. Therefore, this is not recurrent behavior and the suggester at block 126 is not engaged. Instead, execution is transferred directly to junction 127.

Whatever the determination of block 124, control moves to junction 127 and then to block 128. At block 128 a determination is made whether the subject is demonstrating a positive dreaming condition. This condition is satisfied if no movement clusters appear during the approximate dream period. Or equivalently, if no integer values appear in the row or column dimension of the NCYCLE array. In this case, the dream period parameter is approximately 15-30 elements long and is adjustable by manipulating the variable LENGTH, as shown in paragraph nine of the listing. When dream conditions are observed at block 128, the flag is increased by 1 at block 132. If, however, the above conditions are not satisfied, the loop is exited at block 130 and execution is returned to start block 96.

After the flag has been increased at block 132, a determination is made at block 134 whether the flag equals the integer value 3. If the flag does not equal the integer value 3, the subject is experiencing an apparent dream event without confirmation, as in block 20 of system 10. This does not warrant the activation of subject stimuli. Hence, by way of line 135, execution moves to block 136 where a determination is made whether a positive post-dream condition is apparent. If post-dream motion is observed, the flag is increased by 1 and execution moves to junction 119. Since the flag now equals the integer value 2, when block 118 is again executed the NCYCLE array will be referenced in a time slot which is 80-100 minutes greater than when the preceding analysis occurred. The references to the NCYCLE array elements are increased by an integer value between 80 and 100. Since all references made to block 118 are retrospective this confirmation technique references the NCYCLE array to determine what subject motion occurred over the last 80-100 minutes. Therefore, if execution determines negative conditions in blocks 120 and 128, execution returns to start block 96 and MOVTAB values are again assigned.

Referring again to the decision of block 134, if the flag is equal to the integer value 3, a recurrence is established, and system 10a is evidently analyzing the recurrence of an earlier pattern. Thus, by way of line 137, a wakeup parameter is set at block 142. This wakeup parameter establishes an allowable period during which system 10a could confirm the apparent dream event. By referencing block 100 and incorporating the AND gate of block 144, the following condition is established: If a motion is detected, and the wakeup parameter of block 142 is still engaged, the alarm is sounded at block 146. Thus awakening subject 42 and carrying out the present invention on the first post-dream motion of subject 42. If, however, the wakeup parameter expires before a motion is detected, execution returns to start block 96, as shown in paragraph four of the listing.

The operation of dream retrieval system 10a is now described with respect to the control and sequencing of data processor 58 of system 40. The listing for the program for microprocessor 58 appears at the end of the specification as an Appendix and is written in standard FORTRAN-77 understandable by those of ordinary skill in the art. The program begins with variable declarations and sequentially executes all the necessary deductions and functions set forth in system 10a. The main program can be compiled on any computational device which supports FORTRAN-77 and has at least one analog Input/Output conversion port. However, the time conversion subroutine, set forth in the paragraph ten of the listing, is unique to the Digital Equipment Corporation VAX 11/780 under Vms. 3.0 system software and may require alteration for usage on other systems.

Although the invention has been particularly shown and described with reference to a preferred embodiment thereof, it will be understood by those skilled in the art, that various changes may be made therein without departing from the spirit or scope of the invention.

APPENDIX

TABLE OF CONTENTS

1. Introduction.
2. Variable initialization.
3. Dozing routine.
4. Input/Output lines.
5. Program termination.
6. Alarm routine.
7. Motion recording routine.
8. Motion counting routine.
9. Recurrence analysis.
10. Time conversion subroutine.

1) INTRODUCTION

```
*********** THE DREAM RETRIEVAL SYSTEM **********
*
C234567   THROUGHOUT THE PERIOD OF SLEEP, THE
C         EMBODIED SOFTWARE MONITORS AND CORRELATES
C         THE CYCLIC BODY MOVEMENTS INHERENT IN
C         NATURAL SLEEP.  FROM THE UNIQUE BODY
C         MOTIONS WHICH SURROUND DREAM SLEEP AND THE
C         CYCLIC NATURE WITH WHICH THEY OCCUR, THE
C         EMBODIMENT DETERMINES APPROXIMATE LEVELS OF
C         CONSCIOUSNESS AND, MORE SPECIFICALLY, THE
C         LOCATION OF DREAM PERIODS.  BELOW IS A
C         FORTRAN-77 DEPICTION OF THE LOGIC REQUIRED
C         TO ESTABLISH THE SLEEP-DREAM CYCLE.
*
```

2) VARIABLE INITIALIZATION

```
C      DECLARE MOTION RECORDING ARRAYS
*
       DIMENSION MOVTAB(600),NCYCLE(650,2)
*
C      INITIALIZE ALL MOTION RECORDING ARRAYS.
*
       DATA (MOVTAB(I),I=1,600)/600*0/
       DATA ((NCYCLE(I,J),I=1,650),J=1,2)/1300*0/
*
C      THE ARRAY <MOVTAB> (MOVEMENT TABLET) IS THE
C      ARRAY ON WHICH EVERY INCOMING MOTION IS
C      STORED.  EACH ELEMENT OF THE ARRAY IS CON-
```

```
C       SIDERED TO REPRESENT THE BODY ACTIVITY
C       WHICH OCCURED DURING ONE PRECISE MINUTE OF
C       SLEEP.
*
C       THE ARRAY <NYCLE> (NIGHT'S CYCLE) IS THE
C       ARRAY ON WHICH ALL CONFIRMED PRE- AND POST-
C       DREAM MOTION FLURRIES ARE STORED. PRE-
C       DREAM FLURRIES ARE STORED AS BINARY ONES"
C       IN (X,1), WHILE POST-DREAM FLURRIES ARE
C       STORED SIMILARLY IN (X,2). PROJECTED OR
C       "PREDICTED" PRE-DREAM MOTION FLURRIES ARE
C       STORED IN (X,1) AS "BINARY TWOS".
*
```

3) DOZING ROUTINE

```
C       MORE VARIABLE INITIALIZATION NOW FOLLOWS.
C       THE ONLY ONE OF IMPORTANCE NOW IS
C       "IDOZE" WHICH DETERMINES HOW LONG THE
C       PATIENT IS GIVEN (IN MINUTES) TO INITIALLY
C       FALL ASLEEP.
*
        IEXPIR=0
        ICURNT=0
        IDOZE=15
*
C       THE DOZING PARAMETER ELAPSES ITSELF USING
C       THE FUNCTION SUBPROGRAM: "NTIME( )".
C       "NTIME( )" (SUPPLIED BELOW) WAS COMPILED
C       ON A VAX-11/780 RUNNING UNDER VMS V3.0.
C       COMPILATION OF THIS PROGRAM ON DIFFERENT
C       MACHINES MAY REQUIRE SLIGHT MANIPULATION
C       OF THIS SUBROUTINE.
*
  10    IF (NTIME(ICURNT)-IDOZE) 10,20,20
*
```

4) INPUT/OUTPUT ASSIGNMENTS

```
C       INPUT AND OUTPUT STATEMENTS FOLLOW THE
C       ASSIGNMENTS GIVEN:
*
C           LOGICAL NUMBER 10
C              INP:MOTION SENSOR (BINARY ONE)
C           LOGICAL NUMBER 11
C              OUT:ALARM BOX OR SIREN
C           LOGICAL NUMBER 12
C              OUT:TAPE PLAYER
*
  20    READ(10,*) MOVE
*
C       "MOVE" IS THE ONLY INPUT VARIABLE. IT IS
C       OF THE FORM "BINARY ONE" AND IS A DIRECT
C       INPUT FROM THE MOTION SENSING APPARATUS.
*
```

5) PROGRAM TERMINATION

```
C     IF THE PROGRAM HAS RUN FOR MORE THAN 700
C     MINUTES IT WILL AUTOMATICALLY TERMINATE.
*
      IF (NTIME(ICURNT).GT.700) THEN
         GOTO 120
      ENDIF
*
```

6) ALARM ROUTINE

```
      IF (NTIME(ICURNT)-IEXPIR) 30,30,40
*
 30   IF (MOVE.EQ.1) THEN
         WRITE (11,*) ' SOUND ALARM '
      ENDIF
*
C     ALTHOUGH THE ABOVE LINES APPEAR AT THE BE-
C     GINNING OF THE PROGRAM, THEY MARK THE FINAL
C     POINT OF A POSITIVE DREAM TRACKING.  IF THE
C     VALID WAKING PERIOD HAS NOT EXPIRED
C     "IEXPIR", THE ALARM SOUNDS.
*
 40   IEXPIR=0
*
```

7) MOTION RECORDING ROUTINE

```
      IF (MOVE.EQ.1) THEN
         MOVTAB(NTIME(ICURNT))=
     *                    MOVTAB(NTIME(ICURNT))+1
*
C     THE MOVEMENT TABLET IS ASSIGNED VALUES.
*
```

8) MOTION COUNTING ROUTINES

```
      IPREPR=8
      IPRCNT=3
      ICOUNT=0
*
C     THROUGHOUT THIS PART OF THE PROGRAM THE
C     INDICATED PRE-DREAM MOTION FLURRY IS
C     SEARCHED FOR.  THIS IS ACCOMPLISHED BY
C     DETERMINING IF "IPRCNT" MOVEMENTS OCCUR
C     IN "IPREPR" MINUTES.
*
      DO 50 K=NTIME(ICURNT)-IPREPR,
     *                          NTIME(ICURNT)
         ICOUNT=ICOUNT+MOVTAB(K)
 50   CONTINUE
*
      IF (ICOUNT.GE.IPRCNT) THEN
*
         IF (NCYCLE(NTIME(ICURNT),1).EQ.2)
     *                                 THEN
```

```
        WRITE (12,*) ' ENGAGE SUGGESTER '
      ENDIF
*
C     ALTHOUGH THE PRIMARY FUNCTION OF THIS
C     DEVICE IS TO DETERMINE THE COMPLETION
C     OF A DREAM, AT THIS POINT A DREAM IS
C     "IN PROGRESS." HYPNOTIC SUGGESTIONS
C     ARE NOW PLAYED TO USER IN AN ATTEMPT
C     TO ENHANCE OR ALTER THE DREAM CONTENT.
*
      NCYCLE(NTIME(ICURNT),1)=1
*
C     THIS ESTABLISHES PRE-DREAM FLURRIES
C     ON "NCYCLE(X,1)"
*
      ENDIF
*
      IPOSPR=6
      IPOSCT=2
      ICOUNT=0
*
      DO 60 K=NTIME(ICURNT)-IPOSPR,
     *                       NTIME(ICURNT)
         ICOUNT=ICOUNT+MOVTAB(K)
 60   CONTINUE
      IF (ICOUNT.GE.IPOSCT) THEN
         NCYCLE(NTIME(ICURNT),2)=1
      ENDIF
*
C     A SIMILAR PROCESS TO PRE-DREAM MOTION DE-
C     TERMINATION IS NOW INVOKED. POST-DREAM
C     MOTIONS ARE BEING CORRELATED. UNLIKE
C     BEFORE, CONFIRMATIONS ARE BEING STORED IN
C     "NCYCLE (X,2)"
*
              4) RECURRENCE ANALYSIS
*
C     NOW THAT PRE AND POST DREAM MOTION CON-
C     FIRMATIONS HAVE BEEN RECORDED IN THE AR-
C     RAY "NCYCLE," THE LOOP BELOW FUNCTIONS AS
C     A CYCLIC ANALYZER. A PRE-DREAM MOTION
C     FLURRY FOLLOWED BY A PERIOD OF RELATIVELY
C     "MOTION FREE" SLEEP WILL SET "JFLAG."
C     HERE, A POST-DREAM MOTION FLURRY WILL
C     CONFIRM THE FIRST DREAM POSITION. A FLAG
C     WILL BE SET (BINARY TWO) IN THE IN THE
C     "NCYCLE" ARRAY APPROXIMATELY 80-100 ELE-
C     MENTS PAST THE MOST RECENT CONFIRMED
C     DREAM INITIATION. THIS FLAG SERVES AS A
C     PROJECTION PARAMETER, ABOUT WHICH THE SEC-
C     OND DREAM WILL OCCUR. IF 90-100 MINUTES
C     LATER SIMILAR MOTION PATTERNS ARE OBSERVED
C     "JFLAG" IS TRIPPED AGAIN AND "IEXPIR" IS
C     SET. IN EFFECT, ARMING THE AWAKENING
```

```
C        MECHANISM.
*
*
         JFLAG=0
         DO 110 K=NTIME(ICURNT)-110,NTIME(ICURNT)
           IF (NCYCLE(K,1).EQ.1) THEN
              START=K
              LENGTH=15+INT(K/20)
*
C             (K/20) IS A CORRECTION FACTOR WHICH
C             COMPENSATES FOR THE INCREASED LENGTH
C             OF DREAMS AS THE NIGHT PROGRESSES.
*
              STILL=0
              DO 80 J=1,LENGTH
                 DO 70 I=1,2
                    IF(NCYCLE(K+J,1).EQ.1) THEN
                       STILL=1
                    ENDIF
70               CONTINUE
80            CONTINUE
              IF(STILL.EQ.0) THEN
                 JFLAG=JFLAG+1
                 IF (JFLAG.GE.3) THEN
                    IEXPIR=NTIME(ICURNT)+10
                 ENDIF
                 DO 100 L=1,10
                    IF (NCYCLE(K+J+L,2).EQ.1) THEN
                       JFLAG=JFLAG+1
                       DO 90 M=90,100
                          NCYCLE (START+M,1)=2
90                     CONTINUE
                    ENDIF
100              CONTINUE
              ENDIF
              STILL=0
           ENDIF
110      CONTINUE
         ENDIF
         GOTO 20
*
C        NOW, CONTROL IS RETURNED TO THE READ STATE-
C        MENT WHERE, IF "IEXPIR" IS STILL VALID, THE
C        ALARM IS SOUNDED.  IF "IEXPIR" HAS EXPIRED
C        THE SYSTEM WILL SIMPLY CONTINUE READING AND
C        CORRELATING MOVEMENTS.
*
120      STOP
         END
*

10) TIME CONVERSION SUBROUTINE

C234567     TIME CONVERSION SUBROUTINE
*
C        IT SHOULD BE NOTED THAT THE BELOW IS MERELY
```

```
C          MEANS FOR THE MACHINE TO ESTIMATE TIME.  AS
C          NOTED ABOVE THIS METHOD IS UNIQUE TO THE
C          VAX-11/780 AND MIGHT REQUIRE ALTERATION BE-
C          FORE BEING COMPATIBLE WITH OTHER SYSTEMS.
*
C          SIMPLY, A THREE DIGIT NUMBER (IN MINUTES)
C          IS RETURNED TO THE MAIN PROGRAM WHERE
C          A "TIME INITIAL=000"
*
C          A FULL EXPLANATION OF THE SUBROUTINE IS
C          OMITTED.
*
           FUNCTION NTIME(ICURNT)
           CHARACTER BUF
           CALL TIME(BUF)
           NHOUR=INT(BUF(1:2))
           MINUTE=INT(BUF(4:5))
           NSECND=INT(BUF(7:8))
           MINCNV=NHOUR*60+MINUTE+
     *                 INT(REAL(NSECND)/100.+.5)
           IF (ICURNT.EQ.0.0)THEN
              ICRECT=-MINCNV
           ENDIF
           IF (MINCNV+ICRECT) 10,20,20
10         ICRECT=(24*60)+ICRECT
20         ICURNT=MINCNV+ICRECT
           RETURN
           END
```

I claim:

1. A method for confirming the occurrence of dream behavior parameters in a sleeping subject having dream cycles comprising the steps of:
   (a) detecting a first occurrence of dream behavior parameters;
   (b) establishing a predetermined time period after the detection of the first occurrence, the duration of the time period being related to the duration of a dream cycle;
   (c) determining the substantial absence of dream behavior parameters during the predetermined time period;
   (d) detecting a second occurrence of dream behavior parameters after the predetermined time period; and
   (e) confirming the occurrence of a dream only in response to said determination and second occurrence.

2. The method of claim 1 in which step (d) includes the steps of establishing a time window of predetermined duration beginning at the end of the predetermined time period and confirming the occurrence of a dream only in response to the second occurrence during the window.

3. The method of claim 1 including the additional step of awakening the subject after confirming the occurrence of a dream.

4. The method of claim 1 in which steps (a) and (d) include detecting gross body motion.

5. The method of claim 4 in which the step of detecting gross body motion includes detecting a predetermined number of body motions within a predetermined period of time.

6. The method of claim 4 in which the step of detecting gross body motion comprises:
   (a) rustling nuggets in response to gross body motion; and
   (b) converting into electrical energy acoustical energy produced by impacts between the rustled nuggets.

7. The method of claim 1 in which steps (a) and (d) include detecting a plurality of different dream behavior parameters.

8. A system for confirming the occurrence of dream behavior parameters in a sleeping subject having dream cycles comprising:
   (a) means for detecting a first occurrence of dream behavior parameters;
   (b) means for establishing a predetermined time period after the detection of the first occurrence, the duration of the time period being related to the duration of a dream cycle;
   (c) means for detecting a second occurrence of dream behavior parameters after the predetermined time period; and
   (d) means for confirming the occurrence of a dream only in response to said second occurrence.

* * * * *